US009687282B2

(12) United States Patent
Strnad et al.

(10) Patent No.: US 9,687,282 B2
(45) Date of Patent: Jun. 27, 2017

(54) ORTHOPEDIC PLATE HAVING THREADED HOLES FOR LOCKING SCREWS OR PEGS AND NON-THREADED HOLES FOR A VARIABLE AXIS LOCKING MECHANISM

(75) Inventors: Lee A. Strnad, Broadview Hts., OH (US); Amanda Martin, Norton, OH (US); Dustin Ducharme, Stow, OH (US)

(73) Assignee: Orthohelix Surgical Designs, Inc., Medina, OH (US)

( * ) Notice: Subject to any disclaimer, the term of this patent is extended or adjusted under 35 U.S.C. 154(b) by 2641 days.

(21) Appl. No.: 11/879,560

(22) Filed: Jul. 18, 2007

(65) Prior Publication Data
US 2008/0021477 A1    Jan. 24, 2008

Related U.S. Application Data

(60) Provisional application No. 60/831,647, filed on Jul. 18, 2006, provisional application No. 60/880,910, filed on Jan. 17, 2007, provisional application No. 60/780,032, filed on Mar. 7, 2006, provisional application No. 60/779,865, filed on Mar. 7, 2006.

(51) Int. Cl.
*A61B 17/58* (2006.01)
*A61B 17/56* (2006.01)
*A61B 17/80* (2006.01)

(52) U.S. Cl.
CPC ...... *A61B 17/8033* (2013.01); *A61B 17/8047* (2013.01); *A61B 17/8057* (2013.01); *A61B 17/8061* (2013.01)

(58) Field of Classification Search
CPC .......... A61B 17/56; A61B 17/58; A61B 17/68
USPC ...................... 606/280–331, 70, 71
See application file for complete search history.

(56) References Cited

U.S. PATENT DOCUMENTS

| 6,096,040 | A  | * | 8/2000 | Esser ............................ 606/280 |
| 6,575,975 | B2 | * | 6/2003 | Brace et al. ................. 606/86 B |
| 6,623,486 | B1 | * | 9/2003 | Weaver et al. ................ 606/281 |
| 7,137,987 | B2 | * | 11/2006 | Patterson et al. ............ 606/291 |
| 7,704,251 | B2 | * | 4/2010 | Huebner et al. .............. 606/71 |
| 7,766,948 | B1 | * | 8/2010 | Leung .......................... 606/305 |
| 7,780,711 | B2 | * | 8/2010 | Orbay et al. ................. 606/287 |
| 7,785,327 | B1 | * | 8/2010 | Navarro et al. ............... 606/71 |
| 7,794,482 | B2 | * | 9/2010 | Mathieu et al. .............. 606/290 |
| 2004/0153073 | A1 | * | 8/2004 | Orbay ............................ 606/69 |
| 2004/0220570 | A1 | * | 11/2004 | Frigg ............................. 606/69 |
| 2005/0080421 | A1 |  | 4/2005 | Weaver et al. |
| 2006/0004362 | A1 | * | 1/2006 | Patterson et al. .............. 606/69 |

(Continued)

*Primary Examiner* — Christopher Beccia
(74) *Attorney, Agent, or Firm* — Duane Morris LLP

(57) ABSTRACT

An orthopedic plate system comprises a plurality of fasteners such as pegs or screws and a plate having two sets of holes for the fasteners. The first set of at least one hole includes internal threads that receive a fastener having a head which includes external threads that mate with the internal threads of the hole to lock the fastener at a fixed angle relative to the plate. The second set of at least one hole is devoid of internal threads and has a concavely rounded internal surface and which receives a convexly rounded external surface of a locking insert, which receives a variable axis fastener. The variable axis fastener causes the locking insert to expand to lock the variable axis fastener at a selected angle relative to the plate.

22 Claims, 5 Drawing Sheets

(56) References Cited

U.S. PATENT DOCUMENTS

2006/0015104 A1\* 1/2006 Dalton ............................ 606/70
2006/0235399 A1\* 10/2006 Carls et al. ..................... 606/69

\* cited by examiner

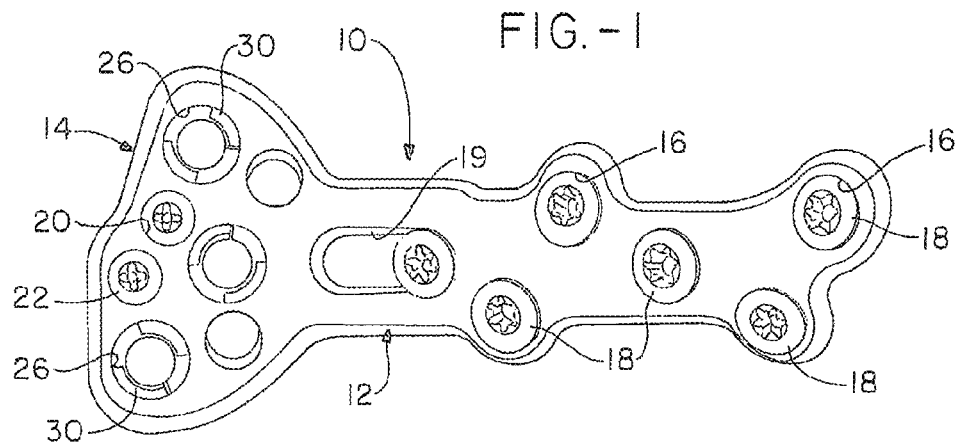
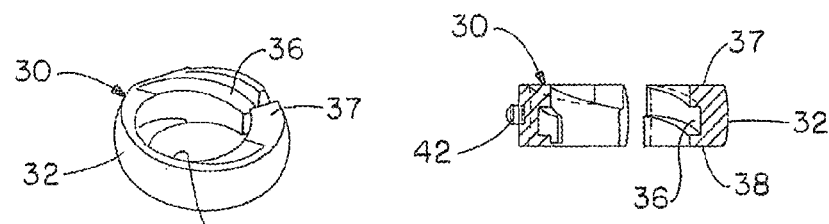
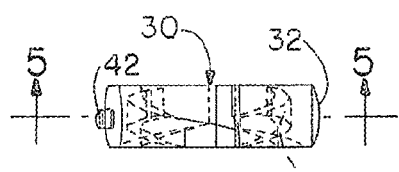
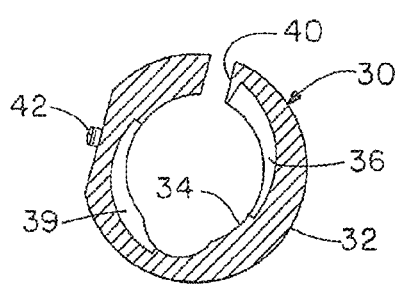
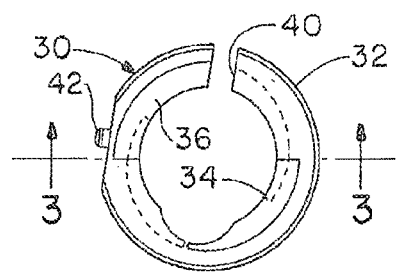
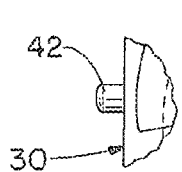
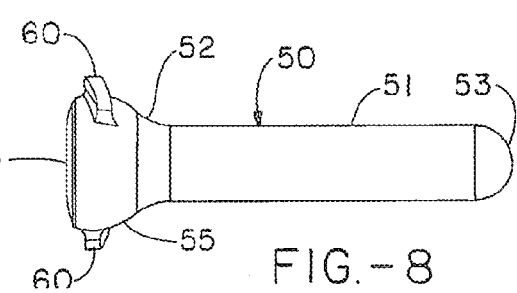

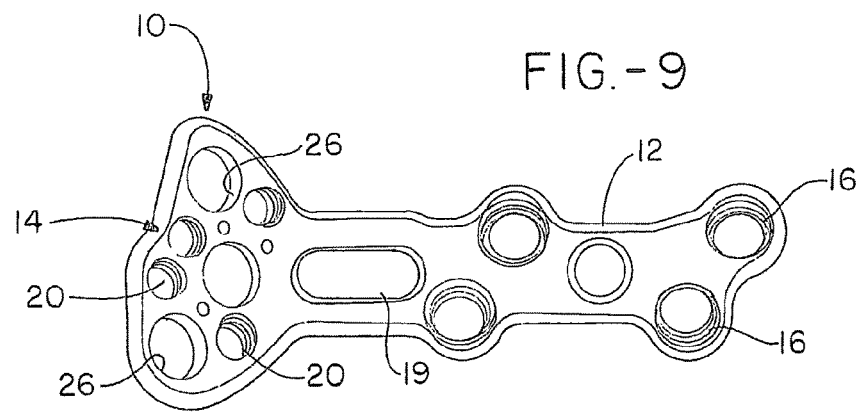
FIG.-9
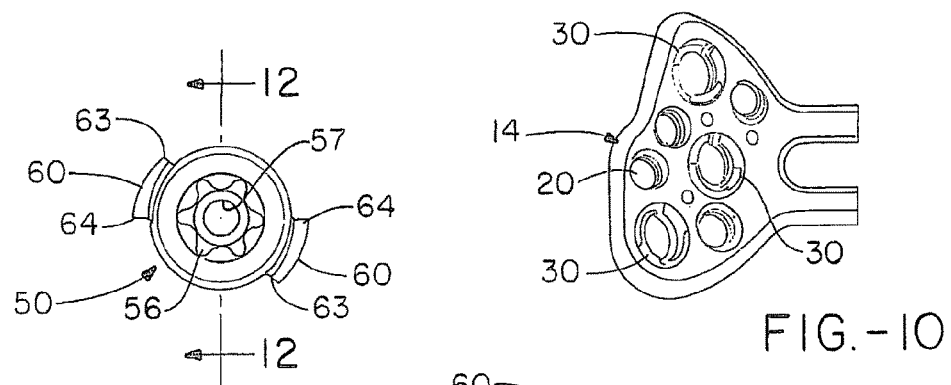
FIG.-10
FIG.-11
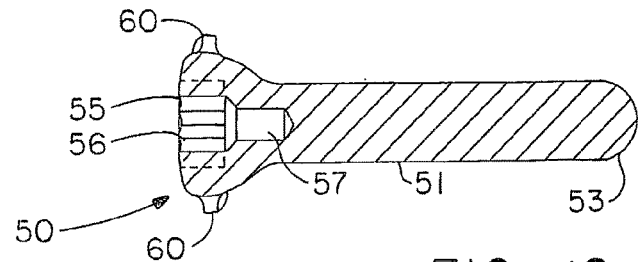
FIG.-12
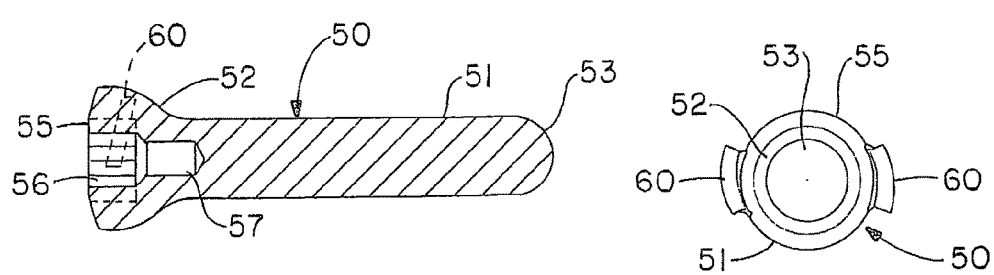
FIG.-13
FIG.-14

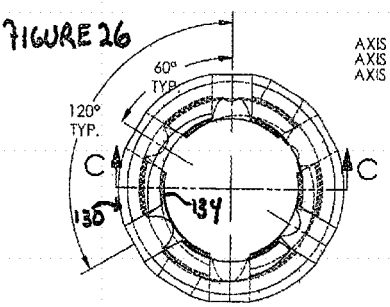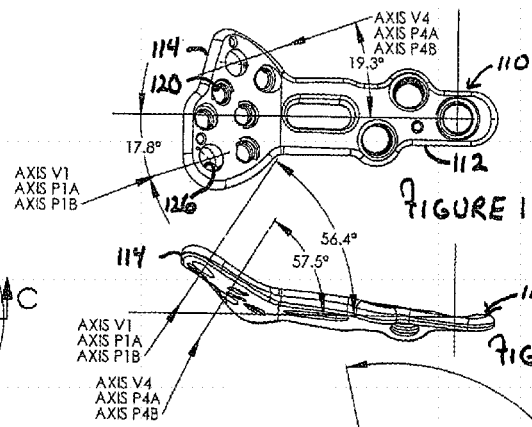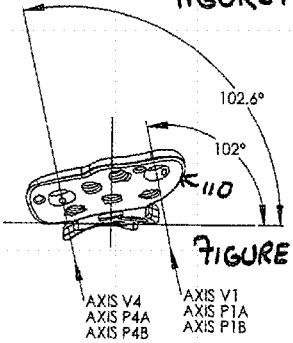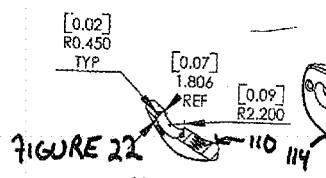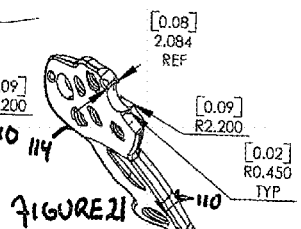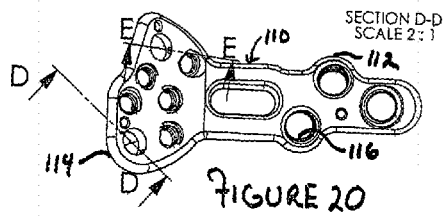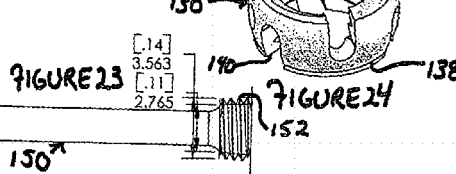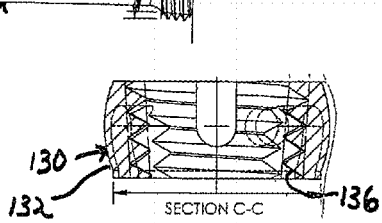

ORTHOPEDIC PLATE HAVING THREADED HOLES FOR LOCKING SCREWS OR PEGS AND NON-THREADED HOLES FOR A VARIABLE AXIS LOCKING MECHANISM

This application is based on U.S. PROVISIONAL APPLICATION Ser. No. 60/831,647, filed on Jul. 18, 2006, U.S. PROVISIONAL APPLICATION Ser. No. 60/880,910, filed on Jan. 17, 2007, U.S. application Ser. No. 11/713,397, filed on Mar. 2, 2007, based on U.S. PROVISIONAL APPLICATION Ser. No. 60/780,032 filed on Mar. 7,2006 and U.S. application Ser. No. 11/713,856, filed on Mar. 5, 2007, based on U.S. PROVISIONAL APPLICATION Ser. No. 60/779,865 filed on Mar. 7, 2006, all herein fully incorporated by reference.

FIELD OF THE INVENTION

The present invention relates to an orthopedic plate and plate system for fixation of bone, and further in particular to an orthopedic plate having holes which receive both fixed angle locking fasteners and variable angle locking fasteners.

BACKGROUND OF THE INVENTION

The design of orthopedic implants has progressed through the development of plates or other stabilization means, including for example rods and or mesh, intended for application to specific bones, and for use with characteristic types of fractures. These plates are optimally designed to correspond to a generalized shape of the bone and further include fixation means, which are generally screws or pegs, that hold the plate to the bone, and further hold fragments of the bone to the plate in association with other fragments so that the fragments will fuse together.

In position on the bone, the plate, fasteners and bone form a construct that accepts dynamic loading. The interaction of the screws or pegs with the bone, and with the plate is a complex matter. Typically, screws include a threaded shaft and pegs may include a threaded shaft or may simply be cylindrical and be devoid of threads about the shaft. Bone has a hard cortical surface and a porous cancellous internal portion and the variable nature of bone must be taken into consideration in the design of an implant system. Further, as bone lives, it reacts to loading and to motion of the fasteners so that threads can loose purchase over time as the bone shifts away from the threads. Further loading between fragments influences fusion of the fragments. Thus, the design of the plate/fastener interface includes considerations of loading as well as accommodation of typical patterns of fragmentation and the intention to capture cortical surfaces and to avoid surrounding soft tissue.

Typically, locking screws or pegs, are locked into a relationship with a plates, and may also lock the bone into that relationship, or in the event that the peg does not include a threaded shaft, the peg may act more as a support for a fragment. Alternatively, if the screw or peg is threaded about its shaft, it may lock the bone fragment, and in the event that the relationship with the plate is not a locking relationship, the fastener may have a certain amount of play relative to the plate, which further accommodates variations in angles that a surgeon may wish to achieve, but which does not inhibit the fastener from backing out of the plate. Fasteners, which lock into the plate, are less likely to back out and provide proud surfaces that could cause irritation to surrounding soft tissue.

There are advantages to providing locking fasteners at selected angles that are designed to capture typical fragments and secure their relationship to the plate. However, it is even more advantageous to provide these locking fasteners with locking fasteners that can be inserted at variable angle and subsequently locked into that position. While other systems have provided locking mechanisms that allow a variable angle fastener to be inserted into a threaded locking hole, these systems do not provide acceptable holding power of the angle of the variable angle fasteners. The present invention meets that need by providing a plate and locking and variable locking fasteners, the plate having a first set of at least one fastener opening that is set in the plate at a selected angle through the plate and that is internally threaded to accept the externally threaded head of a locking fastener, and the plate further having a second set of at least one fastener opening that is not internally threaded, but which has a concavely rounded internal surface that mates with a corresponding convexly rounded external surface of a locking insert at a selected variable angle, the locking insert accepting a fastener and wherein the fastener has means to lock the insert at the selected variable angle relative to the plate. As examples of the locking means, the locking insert may include one or more expansion slots that allow the locking insert to be expanded in the opening in the plate so as to secure it in the plate. More particularly, the locking insert may also include a cam raceway that accepts a camming member on the head of the fastener that causes the locking insert to expand radially, or the locking insert may include internal threads that mate with external threads of the fastener. In this instance, the fastener used in the fixed locking openings may be the same fastener that is used in the variable locking opening, which provides an inventory advantage (it requires fewer fastener types for the surgery).

The present invention can be used in any number of surgical applications, including for example, for small bone plates such as radial plates, tibial plates, and calcaneal plates; for long bone plates, and for the spine or pelvis.

BRIEF DESCRIPTION OF THE DRAWINGS

The invention will be better understood and other features and advantages will become apparent by reading the detailed description of the invention, taken together with the drawings, wherein:

FIG. 1 is a top view of a distal radius plate illustrating an embodiment of the invention having openings for a variable axis locking mechanism assembly and for a fixed axis locking assembly in accordance with the present invention;

FIG. 2 is a perspective view from the top and the side of a locking insert of the present invention;

FIG. 3 is a cross section of the locking insert of FIG. 2 taken along line 3-3 of FIG. 6;

FIG. 4 is a side view of the locking insert of FIG. 2;

FIG. 5 is a cross section of the locking insert taken along line 5-5 of FIG. 4;

FIG. 6 is a top view of the locking insert of FIG. 2;

FIG. 7 is a detail of the stop shown in FIG. 6;

FIG. 8 is a side view of a smooth shaft variable axis locking peg that can be used as part of the locking mechanism assembly of the present invention;

FIG. 9 is a top view of a plate including bores which form a part of the variable axis locking mechanism assembly of the present invention;

FIG. 10 is a top view of the head of the plate of FIG. 9 with the locking inserts in position;

FIG. 11 is a top view of the peg of FIG. 8;

FIG. 12 is a cross section of the peg of FIG. 8 taken along line 12-12 in FIG. 11;

FIG. 13 is a cross section of the peg of FIG. 8 rotated radially 90° from the view of FIG. 12;

FIG. 14 is an end view of the peg of FIG. 8;

FIG. 17 is a top view of a further embodiment of a distal radius plate in accordance with the present invention which illustrates the fixed angles of the fixed axis locking holes;

FIG. 18 is a side view of the distal radius plate of FIG. 17;

FIG. 19 is an edge view of the distal radius plate of FIG. 17;

FIG. 20 is a top view of the distal radius plate of FIG. 17 showing the angles for a different hole;

FIG. 21 is a bottom view of the distal radius plate of FIG. 17 with the plate angled downward;

FIG. 22 is a cross sectional view of the distal radius plate of FIG. 21;

FIG. 23 is a side view of a locking peg that can be used in the fixed angle locking holes or with the variable angle locking mechanism for a further embodiment of the locking mechanism of the present invention;

FIG. 24 is a top angled view of a further embodiment of a locking insert;

FIG. 25 is a cross sectional view of the locking insert of FIG. 24 taken at line U25-25 of FIG. 26;

FIG. 26 is a top view of the locking insert of FIG. 24;

DETAILED DESCRIPTION OF THE INVENTION

Figure 15:
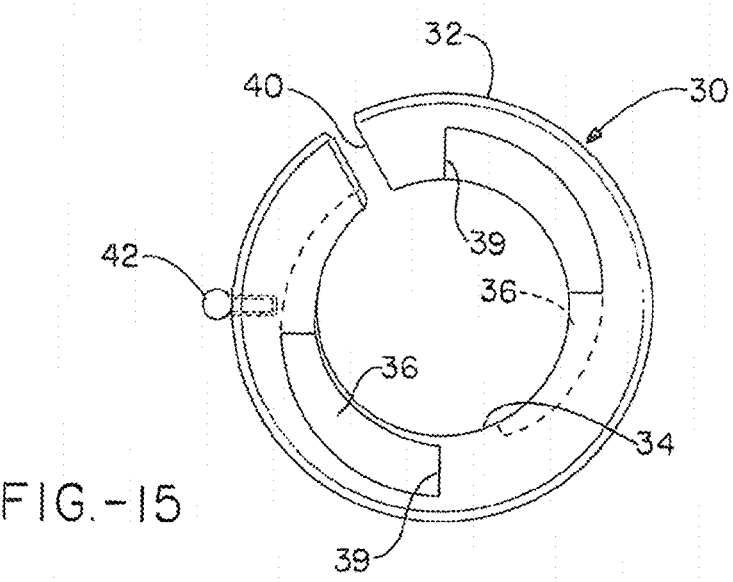
FIG. 15 is a top view of the locking cam insert in the plate and showing the stop recess in phantom.

FIG. 1 shows a variable axis locking mechanism assembly in the distal head portion of a distal radius plate. The plate 10 has a proximal portion 12 connected to a palm shaped head portion 14. The proximal plate portion includes several holes 16 for screws, and a central slot 19. The head 14 includes holes 20 for screws or pegs 22. In particular, there are both fixed angle fasteners, i.e. screws or pegs 24, which can be locking screws which include a threaded head that engages female locking thread in the holes 20 of the plate head. The plate head also includes larger holes 26 that form part of the variable axis locking mechanism of the present invention. These holes 26 are concavely rounded, and preferably partially spherically rounded so that they correspond in shape with the convexly rounded and preferably partially spherically rounded locking cam inserts 30. This allows a rotation of the cam insert 30 in the larger holes of about 30° of conical rotation about a longitudinal axis of the hole 26. The insert as shown in FIGS. 2 through 6, and 15 is a ring shaped insert, having smoothly rounded exterior walls 32, which optionally can include a higher friction surface as is created by knurling, milling or otherwise roughening or texturing the surface. The insert further includes a central opening 34 which has one or more grooves or cam raceways 36. The cam insert 30 has a top surface 37 and a bottom surface 38 which are relatively planar, but include the opening for the cam raceways 36.

Preferably, the cam insert includes 2 cam raceways which begin about 180° from each other and spiral a portion of the way down and around the inside of the cam insert. The cam raceways decrease in the radial dimension from their open starting points on first end as can be seen in FIG. 5. The grooves forming the cam raceways are open, and preferably only for a portion of the top 37 of the insert. This open area of the race allows the cams to be introduced into the race. Subsequently, as the peg is turned in the camming insert, the cam engages the cam race and causes the insert to expand at the gap. This action causes the insert to lock in the recess 26 in the plate which receives the insert.

FIG. 15 illustrates the top openings 39 to the cam raceways 36. Further, the insert 30 has an expansion slot 40 which is essentially a planar slice taken in the insert to create a gap. The gap expands during use to allow the insert to be held in position in the hole by a friction fit. Further, the cam insert 30 includes a stop 42 that resides in a hemispherical well 44 in the hole 26 of the plate. The stop is a projection that is received in the well 44 so as to retain the stop 42 and prohibit the cam insert from turning with the peg as it is turned relative to the plate. This forces the insert to expand the slot 40 to lock it into position.

FIG. 8 illustrates a variable axis locking peg 50 that can be used with the locking mechanism of the present invention. In particular, the peg 50 has a smooth shaft 51 with a rounded or blunt insertion tip 53. The shaft is connected by a neck area 52 to a locking head 55 which may include a torque driving recess 56 with a bore 57 to provide for an interference fit with the post of a torque driver so that the peg is self-retained. The head 55 also includes a pair of tapering flanges or wings 60 which act to engage the cam raceways 36 in the cam insert 30 shown in FIGS. 2 through 6. While the camming mechanism is shown as including only two wings, it should be understood that the head could include more wings, and specifically three or four. The wings extend from about 40° to about 50° and spiral slightly from the base 63 of the head upward toward the top surface 64. The base is slightly rounded. In a preferred embodiment, the wings have a quadrilateral cross section as can be seen in FIG. 12.

FIGS. 9 and 10 illustrate the plate 10 without the inserts 30 in place in the larger holes 26, as well as without the fixed axis pegs in the holes 20. FIG. 10 illustrates the same plate head having three locking cam inserts 30 in the larger holes 26 of the head.

Figure 16:
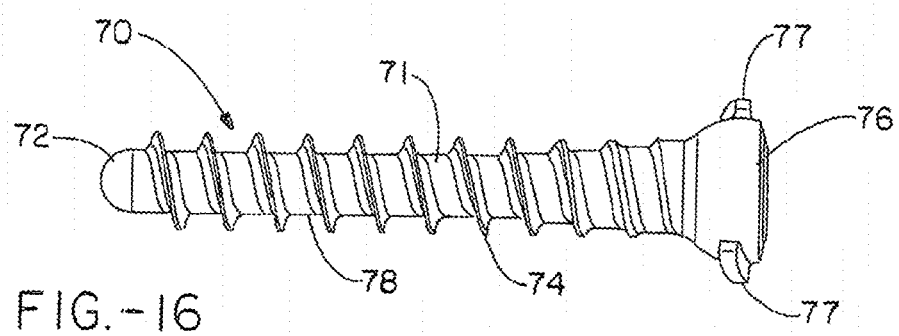
FIG. 16 is a side view of an alternative variable axis locking peg that can be used in the locking mechanism assembly of the present invention.

FIG. 16 shows a variable axis locking screw 70 which is similar to the variable axis locking peg shown in FIGS. 8 and 11 through 14, and has a shaft 71 with a blunt or rounded insertion tip 72. The shaft 71 tapers throughout its length so that the screw 70 does not include a linking neck area as the peg does. The screw does include a locking head 76. The locking head includes a pair of cam wings 77 which are shaped as for the locking peg and which engage the race in the locking insert 30 in the same way as the cam wings of the variable locking peg. The shaft of the variable locking screw 70 is threaded with a thread 74 having a taper to the minor diameter of the shaft while the major diameter 78 does not taper. The head 76 further includes a torque driving recess 79; with an optional bore 80 which retains the screw 70 on the post of a screwdriver.

FIGS. 17 through 22 shows a further embodiment of a distal radius plate in accordance with the present invention. Once again, the plate 110 has a proximal portion 112 connected to a palm shaped head portion 114. The proximal plate portion includes several holes 116 for screws, and a central slot 119. The head 114 includes holes 120 for screws or pegs. In particular, there are both fixed angle fasteners, i.e. screws or pegs, which can be locking screws which include a threaded head that engages female locking thread in the holes 120 of the plate head. The plate head also includes larger holes 126 that form part of the variable axis locking mechanism of the present invention. These holes 126 are concavely rounded, and preferably partially spherically rounded so that they correspond in shape with the convexly rounded and preferably partially spherically rounded locking inserts 130. This allows a rotation of the locking insert 130 in the larger holes of about 30° of conical rotation about a longitudinal axis of the hole 126. The insert as shown in FIGS. 24 through 46, is a ring shaped insert, having smoothly rounded exterior walls 132, which optionally can include a higher friction surface as is created by knurling, milling or otherwise roughening or texturing the surface. The insert further includes a central opening 134 which includes internal threads 136. The locking insert 130 has a top surface 137 and a bottom surface 138 which are relatively planar. The locking insert further includes a plurality of expansion openings 140 (i.e. from 1 to 8, and preferably about 3 to about 6 which are preferably radially spaced about the ring, and preferably which do not extend the entire depth of the insert about it's longitudinal central axis, but which extend about 25 to about 90%, and preferably about 50 to about 75% of the depth of the ring, and further which preferably open in an alternating pattern of up and down relative to the top and bottom of the locking insert. FIG. 23 illustrates a locking fastener, which is in this instance, a non-threaded peg 150 having a shaft and a threaded head 152.

Figure 28:
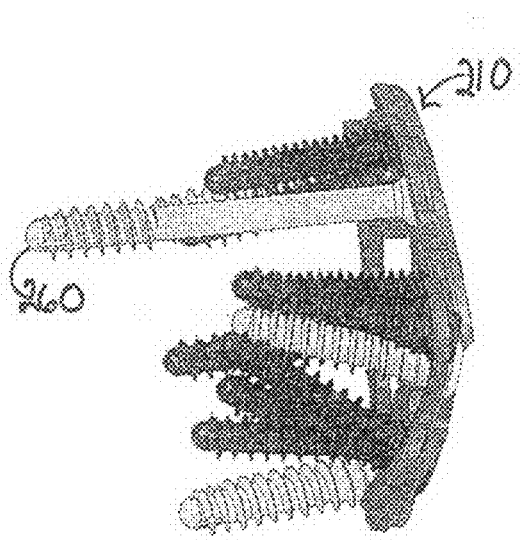
FIG. 28 is a side view of the calcaneal plate of FIG. 27
Figure 27:
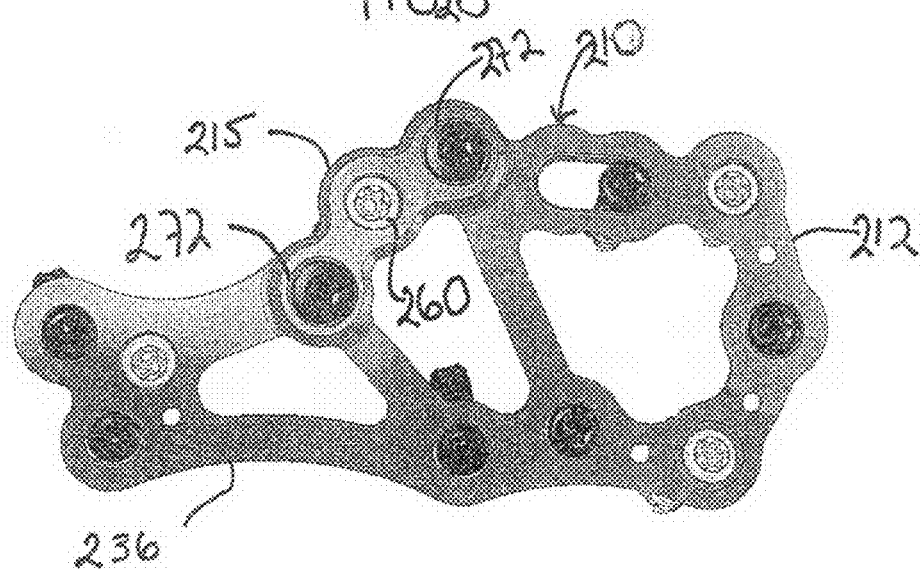
FIG. 27 is a top view of a calcaneal plate in accordance with the present invention.

FIGS. 27 and 28 illustrate a calcaneal plate 210 in accordance with the present invention which has a top outline comprising an anterior tail 236 joined to a blunt ovoid body 212 beginning at an anterior strut and curving through a reinforced three hole portion (i.e., the posterior facet segment) 215 designed to fit just inferior to the posterior facet and which is reinforced to accommodate weight transfer from the tibia to the talus to the calcaneus. The most anterior 211 and the least anterior 213 of the holes in the posterior facet segment 215 may be internally threaded so as to lock the plate to the bone segments in this area at a pre-selected angle or alternatively may include a variable angle locking mechanism 272. The angles of the locking threads are selected to provide scaffolding for the sub-chondral support. The intermediate hole 209 in the posterior facet segment preferably does not include internal threads and is designed to accept screw 260 which is distally threaded and partially devoid of threads in order to generate compression in the bone segment and to allow the sustentaculum to be reduced using the plate. Once again alternatively the intermediate hole may include a variable locking mechanism, in particular if the other two holes are fixed angle locking holes.

While in accordance with the patent statutes the best mode and preferred embodiment have been set forth, the scope of the invention is not limited thereto, but rather by the scope of the attached claims.

What is claimed is:

1. A distal radius plate, comprising: a head portion and a proximal plate portion, the head portion having a palm shaped profile having a complex topography that is substantially free from any planar areas and which has at least one fixed peg hole that is threaded and which defines a fixed angle for a peg which is received in the fixed peg hole and which has at least one variable angle peg hole that has no internal threads and that has a variable angle locking mechanism that permits a variable angle peg to be received in the variable angle peg hole at a variable angle and subsequently to be locked into a desired position.

2. A distal radius plate as set forth in claim 1 in which the variable angle locking mechanism comprises an insert that mates with the at least one variable angle peg hole.

3. A distal radius plate as set forth in claim 2 in which the variable angle peg hole has a longitudinal axis and a concavely rounded wall about the longitudinal axis and the insert is a ring shaped insert having a central opening with a lateral surface and having a convexly rounded side wall and sized to fit in the through opening in the implant at a plurality of angles relative to the longitudinal axis of the through opening.

4. A distal radius plate has set forth in claim 3 wherein the side wall includes at least one opening that allows the radial expansion of the insert and the variable angle peg includes means to cause the radial expansion of the insert.

5. A distal radius plate as set forth in claim 4 wherein the central opening of the insert including at least one raceway in the lateral surface of the central opening, and a fastener that is adapted to extend through the through opening and which includes at least one radially extending expansion member which radially increases along a length thereof and which engages the raceway of the insert whereby the expansion member of the fastener can engage the raceway of the insert to selectively lock the insert at an angle in the through opening relative to the longitudinal axis.

6. A distal radius plate as set forth in claim 4 wherein the means to cause the expansion of the insert is that the insert includes internal threads and the head of the peg includes external threads which mate with the internal threads of the insert.

7. A distal radius plate as set forth in claim 6 wherein the expansion slot extends less than the full depth of the insert.

8. A distal radius plate as set forth in claim 6 wherein there is a first set of at least one expansion slot and a second set of at least one expansion slot and the expansion slot of the first set opens toward the top of the insert and the expansion slot of the second set opens downward.

9. A distal radius plate as set forth in claim 8 wherein there are from about 2 to about 10 expansion slots and the first and second sets of slots alternative about the perimeter of the insert.

10. An orthopedic plate system comprising a plurality of fasteners and a plate having a first surface and a second opposing surface and having a plurality of holes that extend through the plate from the first surface to the second surface, the holes each receiving a fastener, wherein there are two sets of holes, a first set of at least one hole includes internal threads and which receives a fastener having a head which includes external threads that mate with the internal threads of the hole to lock the fastener at a fixed angle relative to the plate, and a second set of at least one hole that is devoid of internal threads and which has a concavely rounded internal surface and which receives a convexly rounded external surface of a locking insert which receives a variable axis fastener that causes the locking insert to expand to lock the variable axis fastener at a selected angle relative to the plate.

11. An orthopedic plate system as set forth in claim 10 wherein locking insert has a central opening with a lateral surface including at least one raceway, and a variable axis fastener that is adapted to extend through the through opening includes at least one radially extending expansion member which radially increases along a length thereof and which engages the raceway of the insert whereby the expansion member of the fastener can engage the raceway of the insert to selectively lock the insert at an angle in the through opening relative to the longitudinal axis.

12. An orthopedic plate system as set forth in claim 11 wherein the means to cause the expansion of the locking insert is that the locking insert includes internal threads and the head of the variable fastener includes external threads which mate with the internal threads of the locking insert.

13. An orthopedic plate system as set forth in claim 10 wherein the locking insert includes at least one expansion slot that extends less than the full depth of the insert.

14. An orthopedic plate system as set forth in claim 13 wherein there is a first set of at least one expansion slot and a second set of at least one expansion slot and the expansion slot of the first set opens toward the top of the locking insert and the expansion slot of the second set opens downward.

15. An orthopedic plate system as set forth in claim 14 wherein there are from about 2 to about 10 expansion slots and the first and second sets of slots alternative about the perimeter of the locking insert.

16. A calcaneal plate system comprising a plurality of fasteners and a plate having a first surface and a second opposing surface and having a plurality of holes that extend through the plate from the first surface to the second surface, the holes each receiving a fastener, wherein there are two sets of holes, a first set of at least one hole includes internal threads and which receives a fastener having a head which includes external threads that mate with the internal threads of the hole to lock the fastener at a fixed angle relative to the plate, and a second set of at least one hole that is devoid of internal threads and which has a concavely rounded internal surface and which receives a convexly rounded external surface of a locking insert which receives a variable axis fastener that causes the locking insert to expand to lock the variable axis fastener at a selected angle relative to the plate.

17. A calcaneal plate system as set forth in claim 16 wherein locking insert has a central opening with a lateral surface including at least one raceway, and a variable axis fastener that is adapted to extend through the through opening includes at least one radially extending expansion member which radially increases along a length thereof and which engages the raceway of the insert whereby the expansion member of the fastener can engage the raceway of the insert to selectively lock the insert at an angle in the through opening relative to the longitudinal axis.

18. A calcaneal plate system as set forth in claim 16 wherein the means to cause the expansion of the locking insert is that the locking insert includes internal threads and the head of the variable fastener includes external threads which mate with the internal threads of the locking insert.

19. A calcaneal plate system as set forth in claim 18 wherein the locking insert includes at least one expansion slot that extends less than the full depth of the insert.

20. A calcaneal plate system as set forth in claim 19 wherein there is a first set of at least one expansion slot and a second set of at least one expansion slot and the expansion slot of the first set opens toward the top of the locking insert and the expansion slot of the second set opens downward.

21. An orthopedic plate system comprising a plurality of fasteners and a plate having a first surface and a second opposing surface and having a plurality of holes that extend through the plate from the first surface to the second surface, the holes each defining a longitudinal axis and receiving a fastener and at least one of the holes including internal threads, wherein there are two sets of fasteners, the first set of fasteners which comprises fixed angle locking fasteners including at least one fastener having a head which includes external threads that mate with the internal threads of the hole to lock the fastener at a fixed angle relative to the plate the fixed angle locking fastener having a fixed angle locking fastener longitudinal axis which coincides with the longitudinal axis of the hole when the fastener is seated in the hole, and the second set of fasteners which comprises variable angle locking fasteners including at least one fastener assembly which comprises a variable angle fastener and a locking insert which locks the variable axis fastener at a selected angle relative to the plate, the variable angle locking fastener having a ring shaped variable angle insert with a variable angle locking fastener axis, and the fastener assembly allowing for the variable angle locking fastener axis to have conical rotation about the longitudinal axis of the hole prior to being locked at a selected fixed angle relative to the longitudinal axis of the hole.

22. An orthopedic plate system as set forth in claim 21 wherein the fastener assembly allows for 30° of conical rotation about the longitudinal axis of the hole prior to being locked at a selected fixed angle relative to the longitudinal axis of the hole.

\* \* \* \* \*